United States Patent [19]

Rokugawa

[11] Patent Number: 4,844,868
[45] Date of Patent: Jul. 4, 1989

[54] AUTOMATIC CHEMICAL ANALYSIS REAGENT DISTRIBUTION AND ANALYSIS APPARATUS

[75] Inventor: Kyuji Rokugawa, Tochigi, Japan

[73] Assignee: Kabushiki Kaisha Toshiba, Kawasaki, Japan

[21] Appl. No.: 872,814

[22] Filed: Jun. 11, 1986

[30] Foreign Application Priority Data

Jun. 18, 1985 [JP] Japan .................................. 60-133544

[51] Int. Cl.⁴ ........................................... G01N 35/04
[52] U.S. Cl. ....................................... 422/64; 422/65; 422/100
[58] Field of Search ........................ 422/64, 65, 63, 67, 422/100, 102; 222/372, 383; 141/27, 258–262, 130

[56] References Cited

U.S. PATENT DOCUMENTS

| | | | |
|---|---|---|---|
| 2,545,319 | 3/1951 | Sundholm | 222/383 |
| 2,572,540 | 10/1951 | Thompson | 222/372 |
| 3,015,415 | 1/1962 | Marsh et al. | 222/383 |
| 3,213,903 | 10/1965 | Armstrong | 222/372 |
| 3,430,813 | 3/1969 | Gilmont | 222/383 |
| 3,644,095 | 2/1972 | Netheler et al. | 141/130 |
| 3,687,632 | 8/1982 | Natelson | 422/65 |
| 3,883,305 | 5/1975 | Hoskins et al. | 422/65 |
| 4,200,607 | 4/1980 | Suzuki | 422/64 |
| 4,306,670 | 12/1981 | Oshikubo | 222/383 |
| 4,322,216 | 3/1982 | Lillig et al. | 422/64 |
| 4,456,152 | 6/1984 | Young et al. | 222/383 |
| 4,501,491 | 2/1985 | Breda et al. | 422/65 |
| 4,664,885 | 5/1987 | Minekane et al. | 436/47 |

FOREIGN PATENT DOCUMENTS 0050659 3/1982 Japan ..................................... 422/65

Primary Examiner—Michael S. Marcus
Attorney, Agent, or Firm—Finnegan, Henderson, Farabow, Garrett, Dunner

[57] ABSTRACT

An analysis apparatus is disclosed, which comprises guide rails for supporting a plurality of sample-containing reaction tubes in a straight row, a plunger for moving the reaction tubes supported on the guide rails in the direction of arrangement, a first rotary table for supporting a plurality of sample-containing reaction tubes along a circular line, and a motor for rotating the rotary table. Second rotary tables are disposed above the straight and circular arrangements of reaction tubes. These second rotary tables support at least two reagent distributors for distributing reagent into the reaction tubes. Each reagent distributor includes a reagent phial containing a reagent and a pump integral with the reagent phial for withdrawing the reagent in the reagent vessel. The pump has a nozzle through which the reagent is discharged. The rotary table is rotated by a motor such that the nozzle of a reagent distributor used for reagent distribution is brought to a position right above a pertinent reaction tube. The pump of the reagent distributor used for the reagent distribution is driven by a plunger.

4 Claims, 4 Drawing Sheets

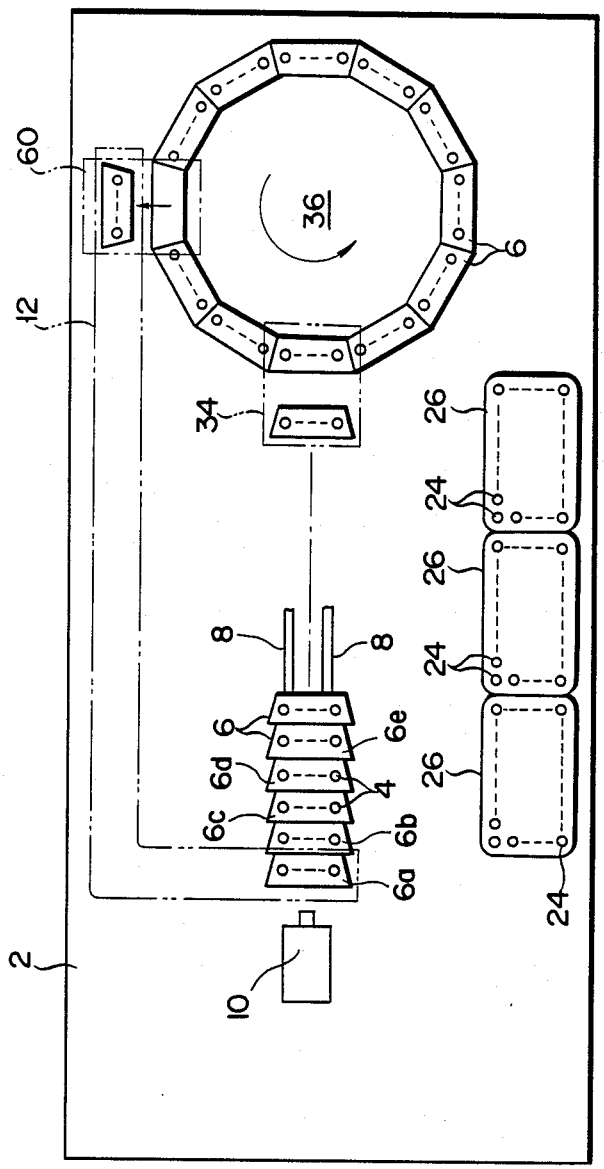

AUTOMATIC CHEMICAL ANALYSIS REAGENT DISTRIBUTION AND ANALYSIS APPARATUS

BACKGROUND OF THE INVENTION

This invention relates to an automatic chemical analysis reagent distributor and analysis apparatus for automatically performing chemical analysis of samples.

In the analysis apparatus of the type noted, it is an essential element to distribute various reagents to reaction tubes containing samples to be analyzed. Heretofore, a pipetting system has been employed for such reagent distribution.

The pipetting system comprises a plurality of reagent phials containing different reagents, a plurality of reaction tubes, and a single reagent distribution nozzle which can move between the phials and the reaction tubes. The reagent distribution nozzle selectively sucks up the reagents from the reagent phials and distributes them to the individual reaction tubes. It takes a long time to distribute each reagent since the distribution nozzle has to be moved between the reaction tubes and the phials. In addition, since one nozzle is used commonly for a plurality of reagents, cross contamination is liable to result.

A dispensing system is also well known in the art, which can solve the above problem. In this system, a plurality of reagent phials containing different reagents and reagent distribution nozzles for the respective reagent phials are interconnected by tubes via pumps. This system can solve the above problem. However, a noticeable dead space is produced in each tube. In addition, the pumps and tubes occupy considerable space, thus leading to size increase of the system.

SUMMARY OF THE INVENTION

An object of the invention is to provide an automatic chemical analysis reagent distributor and analysis apparatus, with which it is possible to eliminate dead space in the reagent passage, reduce size, reduce distribution time and eliminate cross contamination.

According to the invention, there is provided an automatic chemical analysis reagent distributor, which comprises a reagent vessel containing a reagent and a pump for withdrawing the reagent in the reagent vessel, the pump being integral with the reagent vessel and having a nozzle through which the reagent is discharged.

According to another aspect of the present invention, there is provided an analysis apparatus, which comprises moving means for arranging a plurality of sample-containing reaction tubes at least in a row and moving the reaction tubes in the direction of the arrangement, at least two reagent distributors for distributing reagent into the reaction tubes, the reagent distributors each including a circular line, a plurality of reagent vessels provided along the circular line for containing reagents and pumps for withdrawing the reagent in the reagent vessels, each of the pumps being integral with a respective one of the reagent vessels and having a nozzle through which the reagent is discharged, support means for supporting the reagent distributors, rotating means for rotating the support means around the center of the circular line to bring the nozzle of the reagent distributor used for reagent distribution to a position right above a pertinent reaction tube, and driving means for driving the pump of the reagent distributor used for the reagent distribution.

The automatic chemical analysis reagent distributor comprises the reagent vessel and pump integral with the reagent vessel. Thus, no dead space will be formed in the reagent passage, and it is possible to obtain size reduction.

Further, at least two reagent distributors are disposed such that they can be revolved for reagent distribution along reaction tubes arranged at least in a row. Thus, the distribution time can be reduced, and cross contamination will be avoided.

BRIEF DESCRIPTION OF THE DRAWINGS

FIGS. 1 to 5 show an embodiment of the invention, in which:

FIG. 1 is a schematic front view showing an analysis apparatus;

FIG. 2 is a plan view showing the same apparatus;

FIG. 3 is a plan view showing a reaction tube cassette;

FIG. 4 is a perspective view showing a reagent distributor;

FIG. 5 is a sectional view showing a check valve; and

DETAILED DESCRIPTION OF THE PREFERRED EMBODIMENTS

Now, an embodiment of the invention will be described with reference to FIGS. 1 to 5.

Figure 1:
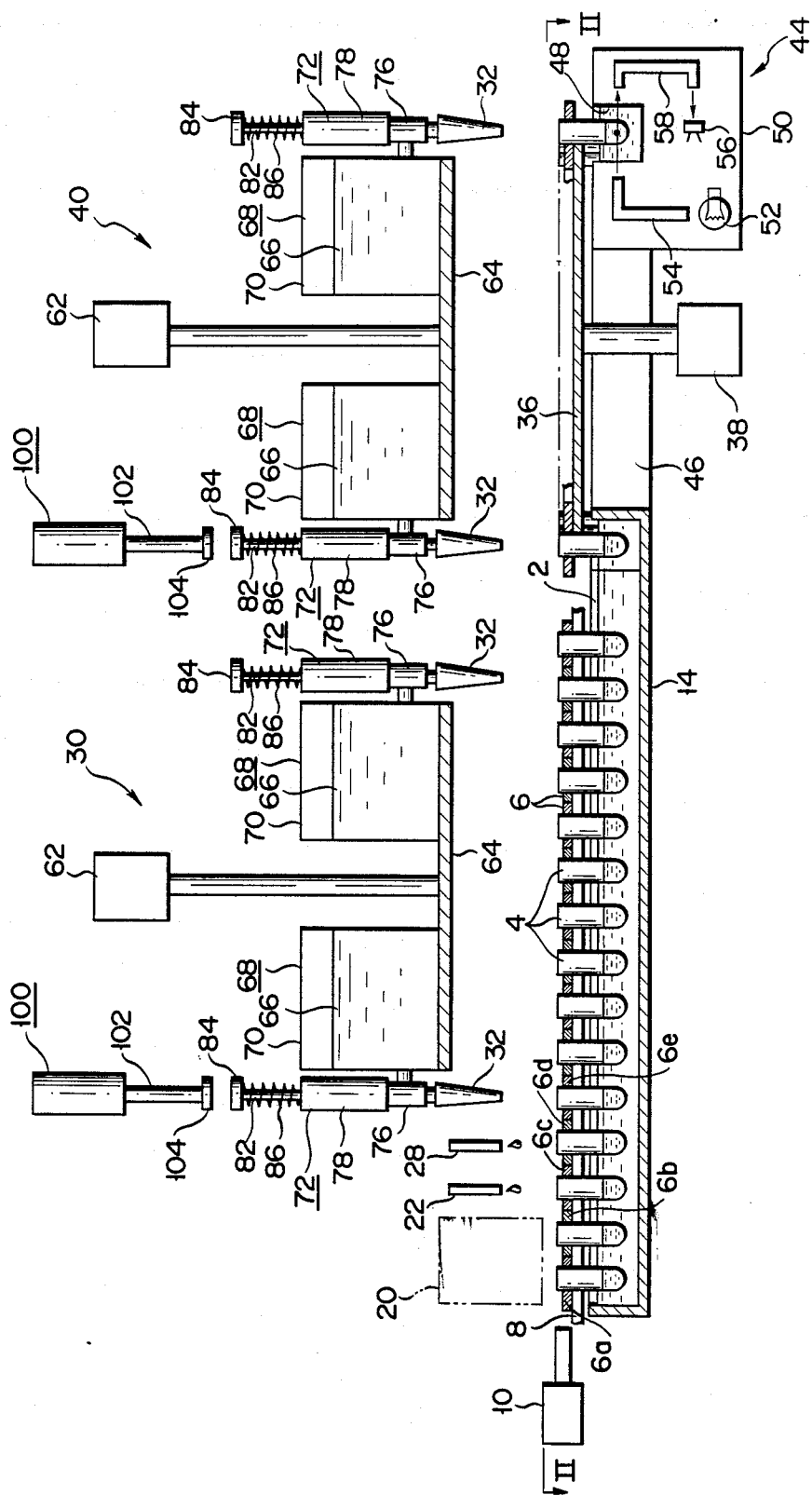

Referring to FIGS. 1 and 2, reference numeral 2 designates a base. Base 2 has a pair of horizontal and straight guide rails 8, along which trapezoidal reaction tube cassettes 6 each holding a plurality of reaction tubes 4 are guided. Feed plunger 10 is disposed to face one end of rails 8. Each reaction tube cassette 6 is conveyed by conveying mechanism 12 (shown schematically in FIG. 2 and to be described later in detail) to a first cassette position at the end of guide rails 8 facing plunger 10 noted above. When reaction tube cassette 6 is brought to this first cassette position (filled by cassette 6a in FIGS. 1 and 2), plunger 10 is driven for one stroke, feeding reaction tube cassettes 6 by a predetermined pitch toward the other end of guide rails 8. More specifically, trapezoidal reaction tube cassettes 6 are arranged in a row on guide rails 8 with their short side directed forwards in the direction of the feed, and they are fed intermittently at a predetermined pitch. As shown in FIGS. 1 and 2, reaction tube cassettes 6a through 6e occupy the first through fifth cassette positions. First temperature controller 14 is disposed underneath guide rails 8. Controller 14 is a straight, long member extending along guide rails 8. Reaction tubes 4 which are held in individual reaction tube cassettes 6 are fed while their temperatures are controlled by first temperature controller 14. As shown in FIG. 3, each reaction tube cassette 6 holds a plurality of reaction tubes 4 arranged along an arcuate line 16 of a predetermined radius. Reaction tube cassette 6 also has a pair of pin holes 18 formed near the opposite ends.

Rinsing/drying station 20 for rinsing and drying reaction tubes 4 is disposed right above the first and second cassette positions in the intermittently fed row, occupied by first and second reaction tube cassettes 6a and 6b in the FIGS. 1 and 2. Sampling nozzle 22 is positioned right above the third cassette position, occupied by third reaction tube cassette 6a in FIGS. 1 and 2.

Sampling nozzle 22 is capable of movement in horizontal and vertical directions between the position right above third reaction tube cassette 6c and a position right above sample cassettes 26, each of which is provided in a temperature controller (not shown) and holds a plurality of sample vessels 24. Sample nozzle 22 is adapted to suck up a sample from given sample vessel 24 and distribute it into reaction tubes 4 in reaction tube cassette 6 at the position noted above. Sample cassettes 26 are disposed such that they are movable along guide rails 8.

Diluting water nozzle 28 for pouring diluting water into reaction tubes 4 is disposed right above the fourth cassette position, occupied by fourth reaction tube cassette 6d in FIGS. 1 and 2. Nozzle 32 of first reagent distribution mechanism 30 to be described later in detail is located right above the fifth cassette position, occupied by fifth reaction tube cassette 6e in FIGS. 1 and 2. An area occupied by reaction tube cassettes 6 to the right of the sixth cassette position as seen in FIGS. 1 and 2, over which area each reaction tube cassette 6 is fed, constitutes a reaction area to provide for time, during which the reaction between sample and reagent proceeds.

First rotary table 36 is provided at that end of guide rails 8 which is opposite to plunger 10, and is close to first transfer mechanism 34 (shown schematically in FIG. 2). First transfer mechanism 34 transfers each reaction tube cassette 6 from guide rails 8 to an edge portion of first rotary table 36. The edge portion of first rotary table 36 is provided with pins (not shown). Reaction tube cassettes 6 are supported on the edge portion of first rotary table 36, with the pins fitted in the pin holes 18 of the reaction tube cassettes. Reaction tubes 4 are thus arranged on first rotary table 36 such that a circle is formed by successive arcuate lines 16 along which reaction tubes 4 are arranged in reaction tube cassettes 6. Thus the reaction tubes are fed along a circle as first rotary table 36 is driven by drive motor 38.

Nozzle 32 of second reagent distribution mechanism 40 is located right above a portion of first rotary table 36, in which reaction tube cassette 6 is received when transferred by first transfer mechanism 34. Light measurement system 44 and second temperature controller 46 are disposed beneath first rotary table 36. Light measuring system 44 has housing 50, which is provided with groove 48, along which a bottom portion of each reaction tube 4 can proceed. Light source 52 is disposed in housing 50. Light emitted from light source 52 is guided by first optical fiber lightguide 54 to reaction tube 4 found in groove 48. Light transmitted through reaction tube 4 is guided by second optical fiber lightguide 58 to light detector 56. Second temperature controller 46 comprises a fluid-filled circular trough that extends along the circular arrangement of reaction tubes 4 arranged on first rotary table 36. Second temperature controller 46 communicates with the end of first temperature controller 14. Groove 48 of light measurement system 44 is coincident with the trough of second temperature controller 46.

An inlet end of conveying mechanism 12 faces an edge portion of first rotary table 36 via second transfer mechanism 60 (shown schematically in FIG. 2). Second transfer mechanism 60 transfers each reaction tube cassette 6 supported in first rotary table 36 over to conveying mechanism 12. Conveying mechanism 12 conveys each reaction tube cassette 6 transferred from first rotary table 36 by second transfer mechanism 60 to the first cassette position at the end of guide rails 8 faced by plunger 10.

Figure 4:
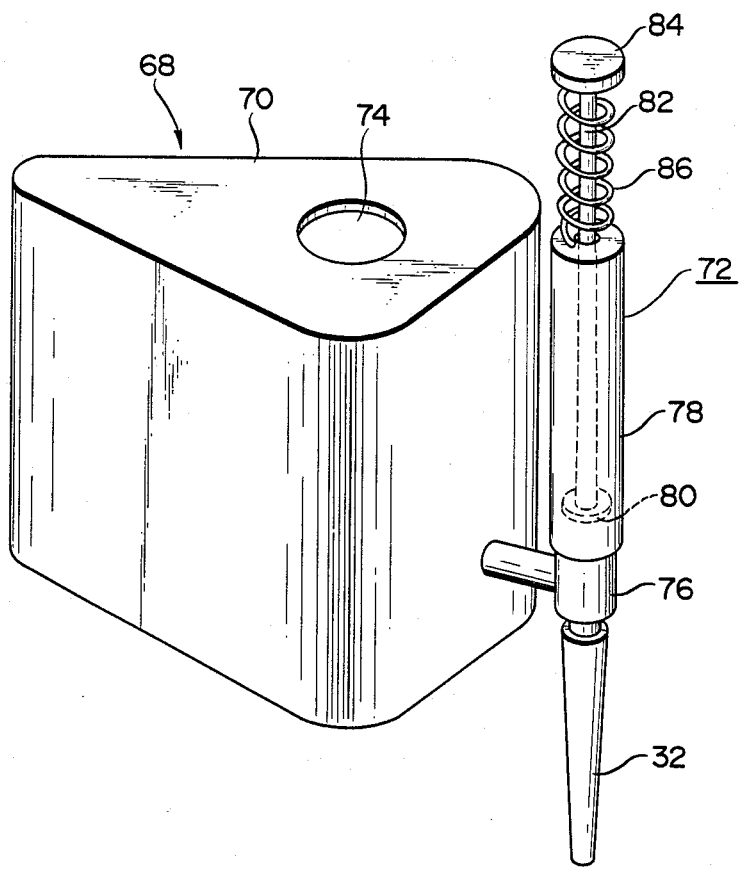
Figure 5:
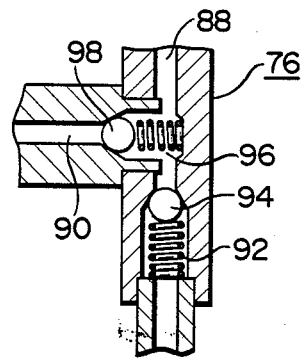

First reagent distribution mechanism 30 is provided above the reaction area where reaction tube cassettes 6 are supported on guide rails 8. Second reagent distribution mechanism 40 is disposed above first rotary table 36. First and second reagent distribution mechanisms 30 and 40 each has second rotary table 64 driven by drive motor 62. Secured to each second rotary table 64 are a plurality of reagent distributors 68 for distributing different reagents. Each reagent distributor 68, as shown in FIG. 4, includes reagent phial 70 containing reagent 66 and pump 72 for withdrawing reagent 66 in reagent phial 70. Reagent phial 70 has, for example, a substantially triangular sectional profile, and has reagent supply hole 74 formed at the top. Pump 72 has check valve 76 secured to the wall of reagent phial 70, cylindrical member 78 secured to and extending upright from check valve 76 and nozzle 32 secured to and extending downward from check valve 76. Piston 80 is provided for reciproval movement in cylindrical member 78. Secured to piston 80 is piston rod 82 projecting from the top of cylindrical member 78. Piston rod 82 has receiving member 84 secured to its top. Coil spring 86 is fitted around piston rod 82 between receiving member 84 and top of cylindrical member 78. Piston 80 is biased upwardly by spring 86. Check valve 76, as shown in FIG. 5, has first passage 88 communicating with the interior of cylindrical member 78 and interior of nozzle 32 and second passage 90 communicating with first passage 88 and the interior of reagent phial 70. Provided in first passage 88 is valve body 94, which is biased by spring 92 to close first passage 88 at a position thereof on the nozzle side of the junction between first and second passages 88 and 90. Provided in second passage 98 is second valve body 98, which is biased by spring 96 to close second passage 90. When piston 80 is moved upwards, second valve member 98 opens second passage 90 against the biasing force of spring 96, while first valve body 94 closes first passage 88 by virtue of the biasing force of spring 92. As a result, reagent 66 in reagent phial 70 is withdrawn into cylindrical body 78. When piston 80 is moved downwards, first valve body 94 opens first passage 88 against the biasing force of spring 92, while second valve body 98 closes second passage 90 by the biasing force of spring 96. As a result, reagent 66 in cylindrical member 98 is discharged from nozzle 32.

With reagent distributor 68 having the above construction, the bottom of each reagent phial 70 is secured to the top of its respective second rotary table 64, and nozzle 32 of each pump 72 is positioned outside the edge of its respective second rotary table 64. With rotation of second rotary table 64, each nozzle 32 executes revolution with the same radius of curvature as that of arcuate line 16 along which reaction tubes 4 in each reaction tube cassette 6 are arranged.

Plunger 100 of first reagent distribution system 3 is disposed right above the fifth cassette position along guide rails 8, occupied in FIGS. 1 and 2 by fifth reaction tube cassette 6e. Plunger 100 of second reagent distribution system 40 is disposed right above the portion of first rotary table 36 in which reaction tube cassette 6 is received when transferred by first transfer mechanism 34. Each of plungers 100 serves to push down piston 80 of the pump 72 disposed beneath it by urging receiving member 84 of pump 72 downward against spring 86. Plunger 100 has actuator 102, which is provided at the lower end with urging member 104 having an increased dimension so that it can urge receiving member 84 of pump 72 downward when nozzle 32 of pump 72 is positioned right above any one of a plurality of reaction tubes 4 held in the reaction tube cassette 6 positioned below plungers 100.

The operation of the above construction will now be described.

Reaction tube cassettes 6 are conveyed one after another by conveying mechanism 12 to the end of guide rails 8 faced by plunger 10. Each reaction tube cassette 6 brought to the end of guide rails 8 noted above is fed intermittently toward first transfer mechanism 34 by plunger 10. At rinsing/drying station 20, reaction tubes 4 held in reaction tube cassettes 6 at the first and second cassette positions are rinsed and dried. Then, a given sample is distributed to reaction tubes 4 by sampling nozzle 22 when reaction tube cassette 6 is at the third cassette position. Then, diluting water is distributed by diluting water nozzle 28 when reaction tube cassette 6 is at the fourth cassette position. Thereafter, at the fifth cassette position, given reagent 66 is distributed by reagent distributor 68 of first reagent distribution system 30. At this time, after nozzle 32 of reagent distributor 68 containing given reagent 66 has been brought to a position right above each reaction tube 4 with rotation of first rotary table 64, piston 80 is pushed down by plunger 100, whereby reagent 66 is poured from cylindrical member 78 of pump 72 into reaction tube 4. When the push-down operation of plunger 100 is completed, piston 80 is raised back by the biasing force of spring 86. At this time, reagent 66 in reagent phial 70 is withdrawn into cylindrical member 78.

Subsequently, reaction tube cassette 6 is fed toward first transfer mechanism 34 at the right end of guide rails 8 as seen in FIGS. 1 and 2. During this time, reaction between sample and reagent 66 in each reaction tube 4 proceeds. Afterwards, reaction tube cassette 6 is transferred by first transfer mechanism 34 from guide rails 8 over to a vacant portion of first rotary table 36 where no reaction tube cassette 6 is supported. Transferred reaction tube cassette is intermittently fed with intermittent rotation of first rotary table 36. During this course, a different reagent 66 is distributed by second reagent distribution mechanism 40 in the manner as in the reagent distribution by first reagent distribution mechanism 30 in accordance with the extent of progress of reaction between reagent 66 and sample in reaction tube 4. In a case where it is desired to secure a long reaction time between the reagent distribution by first reagent distribution mechanism 30 and the reagent distribution by second reagent distribution mechanism 40, several revolutions of reaction tube cassette 6 are caused by first rotary table 36 before distribution of second reagent 66 is done. If there is no need of securing long reaction time, distribution of second reagent 66 is done as soon as reaction tube cassette 6 is transferred over to first rotary table 36 by first transfer mechanism 34. If there is no need of second reagent distribution, it is not done. As each intermittently fed reaction tube 4 passes through groove 48 of light measurement system 44, transmitted light is measured. Measurement data is displayed on a CRT display (not shown) or printed out by a printer to be used for diagnosis. After intended light measurement is over, reaction tube cassette 6 is transferred over to conveying mechanism 12 by second transfer mechanism 60 to be conveyed by conveying mechanism 12 to the first cassette position at the end of guide rails 8 faced by plunger 10.

Each automatic chemical analysis reagent distributor 68 has reagent phial 70 and pump 72 which are integral with each other. Thus, there is no possibility of formation of dead volume in the reagent passage, and also it is possible to obtain size reduction.

Further, a plurality of reagent distributors are provided for revolution over a straight row of reaction tubes 4 and a circular row of reaction tubes 4 so that reagent 66 is distributed by nozzle 32 of the pertinent reagent distributor 68 held right above the pertinent reaction tube 4. Thus, the distribution requires less time, and also cross contamination will never occur.

Figure 6:
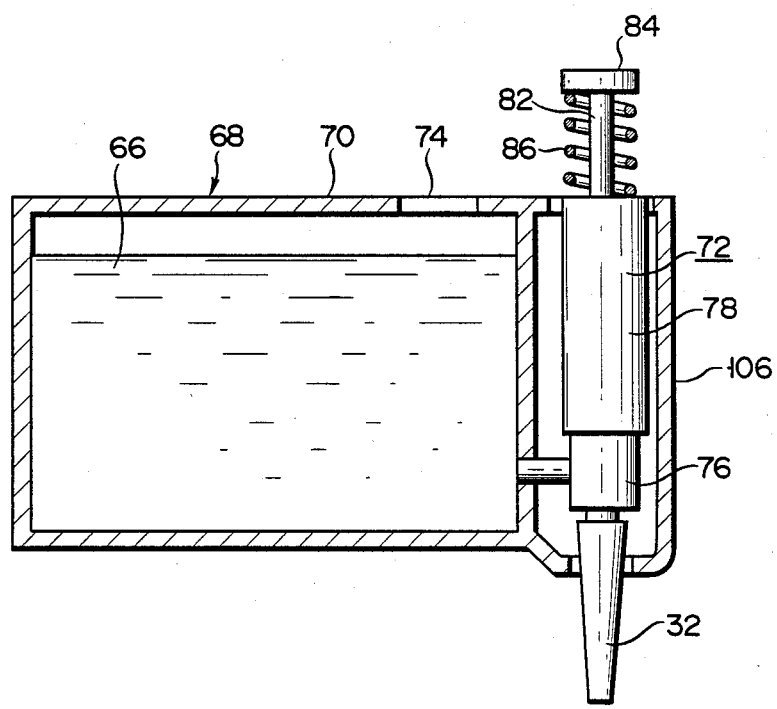
FIG. 6 is a sectional view showing a modification of the reagent distributor.

FIG. 6 shows a modification of reagent distributor 68. In this instance, pump 72 is partly covered by cover 106 secured to the wall of reagent phial 70. With this modification, it is possible to protect pump 72 from external forces. In FIG. 6, parts like those shown in FIG. 4 are designated by the same reference numerals, and are not described in detail.

What is claimed is:

1. An automatic chemical analysis apparatus, comprising:
   a. a plurality of tube holders each holding a plurality of reaction tubes for containing samples to be tested, said reaction tubes being arranged in each of said tube holders along a predetermined filling path, said filling path comprising an arc of an imaginary circle of a predetermined radius, said tube holders being arranged in at least one row along a conveying line;
   b. means for intermittently advancing said tube holders between preselected holder positions along said conveying line, one of said holder positions being a sampling position and another of said holder positions being a reagent supply position;
   c. at least one sample holder for holding a sample;
   d. means for transferring said sample from said sample holder to said reaction tubes of that one of said tube holders which is positioned at said sampling position;
   e. at least one set of a plurality of distributor units for distributing reagents into said reaction tubes, each of said distributor units including a reagent vessel for containing a reagent, a reagent nozzle in flow communication with said reagent vessel, and pump means connected between said reagent vessel and said reagent nozzle for withdrawing and transferring a preselected volume of reagent from said reagent vessel to said reagent nozzle from which reagent is dispensed, said distributor units being movable relative to said conveying line, said at least one set of distributor units being mounted on a rotary table disposed above said tube holders and having an axis of rotation, each of said reagent nozzles of said at least one set of distributor units being spaced from said axis of rotation by a distance substantially equal to said predetermined radius of said imaginary circle;
   f. means for selectively displacing said distributor units relative to said conveying line to cause said reagent nozzle of a selected one of said distributor units to move along said filling path of said tube holder positioned at said reagent supply position in selective alignment above a desired one of said reaction tubes of said tube holder in said reagent supply position, said displacing means rotating said rotary table about said axis of rotation to cause said reagent nozzle of said selected distributor unit to align with said desired reaction tube; and g. a driving member positioned in fixed relation with respect to said reagent position for actuating the corresponding pump device of said selected distributor unit having its respective reagent nozzle in alignment with said desired one of said reaction tubes to discharge the reagent of said selected distributor unit into said desired reaction tube.

2. The apparatus of claim 1, wherein said pump means of each of said distributor units includes:

a cylindrical member;

a piston reciprocably movable in a forward direction and a return direction within said cylindrical member;

a piston rod having a first end connected to said piston and a second end extending out of said cylinder member, said second end including a receiving portion, said receiving portion being constructed and arranged for engagement by said driving member when its respective nozzle is aligned with said desired reaction tube to discharge reagent from said selected distributor unit into said desired reaction tube;

valve means for permitting flow of reagent from said reagent vessel of said respective distributor unit to said cylindrical member at times when said piston moves in said return direction and for permitting flow of reagent from said cylindrical member into said reagent nozzle from which it is dispensed at times when said piston moves in said forward direction; and spring means for biasing said piston in said return direction.

3. The apparatus of claim 2, wherein:

said receiving portion of each of said piston rods is spaced from said axis of rotation of said rotary table by a distance substantially equal to said predetermined radius of said imaginary circle; and said drive member is spaced from said axis of rotation of said rotary table by a distance substantially equal to said predetermined radius of said imaginary table.

4. An automatic chemical analysis apparatus, comprising:

a. a plurality of tube holders each holding a plurality of reaction tubes for containing samples to be tested, said reaction tubes being arranged in each of said tube holders along a predetermined filling path comprising an arc of an imaginary circle having a predetermined radius, said tube holders being arranged in a row along a conveying line having a first end and a second end;

b. a first rotary table positioned adjacent said second end of said conveying line, said first rotary table having a first axis of rotation and a peripheral edge and including means for holding at least one of said tube holders on said peripheral edge with said reaction tubes of said at least one tube holder being spaced from said first axis of rotation by a distance substantially equal to said predetermined radius of said imaginary circle;

c. means positioned adjacent said first end of said conveying line for intermittently advancing said tube holders between preselected holder positions along said conveying line toward said second end thereof, one of said holder positions being a sampling position, another of said holder positions being a first reagent supply position, and a third one of said holder positions being a second reagent supply position located at said peripheral edge of said first rotary table;

d. at least one sample holder for holding a sample;

e. means for transferring a sample from said sample holder to the reaction tubes of that one of said tube holders which is positioned at said sampling position;

f. first reagent distribution means for distributing reagents to the reaction tubes of that one of said tube holders which is positioned at said first reagent supply position, said first reagent distribution means including:

a plurality of first distributor units positioned and arranged for selectively distributing reagents into said reaction tubes located at said first reagent supply position, each of said first distributor units including a first reagent vessel for containing a reagent, a first reagent nozzle in flow communication with said first reagent vessel, and first pump means connected between said first reagent vessel and said first reagent nozzle for withdrawing and transferring a preselected volume of reagent from said first reagent vessel to said first reagent nozzle from which it is dispensed, said first distributor units being mounted on a second rotary table disposed above said tube holders and having a second axis of rotation, each of said first reagent nozzles being spaced from said second axis of rotation by a distance substantially equal to said predetermined radius of said imaginary circle, means for selectively rotating said second rotary table about said second axis of rotation to cause said first reagent nozzle of a selected one of said first distributor units to move along said filling path of that one of said tube holders which is positioned at said first reagent position in selective alignment above a desired one of said reaction tubes of said one of said tube holders which is positioned at said first reagent supply position, and a first driving member positioned in fixed relation with respect to said first reagent position for actuating said pump device of said selected first distributor unit having said respective first reagent nozzle in alignment with said desired reaction tube at said first reagent position to discharge reagent of said selected first distributor unit into said desired reaction tube; and g. second reagent distribution means for distributing reagents to the reaction tubes of that one of said tube holders which is positioned at said second reagent position, said second reagent distribution means including:

a plurality of second distributor units positioned and arranged for selectively distributing reagents into said reaction tubes located at said second reagent supply position, each of said second distributor units including a second reagent vessel for containing a reagent, a second reagent nozzle in flow communication with said second reagent vessel, and second pump means connected between said second reagent vessel and said second reagent nozzle for withdrawing and transferring a preselected volume of the reagent from said second reagent vessel to said second reagent nozzle from which it is dispensed, said second distributor units being mounted on a third rotary table disposed above said tube holders and having a third axis of rotation coincident with said first axis of rotation of said first rotary table, each of said second reagent nozzles being spaced from said third axis of rotation by a distance substantially equal to said predetermined radius of said imaginary circle, means for selectively rotating said third rotary table about said third axis of rotation to cause said second reagent nozzle of a selected one of said second distributor units to move along said filling path of that one of said tube holders which is positioned at said second reagent position in selective alignment above a desired one of said reaction tubes of said one of said tube holders which is positioned at said second reagent supply position, and a second driving member positioned in fixed relation with respect to said second reagent position for actuating said pump device of said selected second distributor unit having said respective second reagent nozzle in alignment with said desired reaction tube at said second reagent position to discharge the reagent of said selected second distributor unit into said desired reaction tube.

* * * * *